United States Patent
Hirai et al.

[11] Patent Number: 5,976,889
[45] Date of Patent: Nov. 2, 1999

[54] GAS ANALYZER AND METHOD FOR DETECTING $NO_x$

[75] Inventors: Hitoshi Hirai; Masaru Miyai, both of Miyanohigashi-machi, Japan

[73] Assignee: Horiba Ltd., Kyoto, Japan

[21] Appl. No.: 08/947,012

[22] Filed: Oct. 8, 1997

[30] Foreign Application Priority Data

Nov. 13, 1996 [JP] Japan .................................. 8-318776

[51] Int. Cl.⁶ .................................................. G01N 21/76
[52] U.S. Cl. ...................... 436/116; 436/117; 436/118; 436/155; 436/158; 436/159; 436/160; 436/172; 436/179; 422/52; 422/82.08; 73/23.31
[58] Field of Search .................................. 436/116, 117, 436/118, 155, 158, 159, 160, 172, 179; 422/82.08, 52; 73/23.31

[56] References Cited

U.S. PATENT DOCUMENTS

| | | | |
|---|---|---|---|
| 3,659,100 | 4/1972 | Anderson et al. | 250/71 R |
| 3,904,371 | 9/1975 | Neti et al. | 23/232 R |
| 3,963,928 | 6/1976 | Zolner | 422/52 |
| 3,967,933 | 7/1976 | Etess et al. | 23/232 E |
| 3,996,008 | 12/1976 | Fine et al. | 23/254 R |
| 4,257,777 | 3/1981 | Dymond et al. | 436/116 |
| 4,333,735 | 6/1982 | Hardy et al. | 23/232 R |
| 4,335,073 | 6/1982 | Sherwood et al. | 422/83 |
| 4,555,931 | 12/1985 | Amimoto et al. | 73/23.31 |
| 4,822,564 | 4/1989 | Howard | 436/116 |
| 4,974,453 | 12/1990 | Hohorst | 73/863.11 |
| 5,358,874 | 10/1994 | Tsurumi | 422/52 |
| 5,453,625 | 9/1995 | Lawson et al. | 250/459.1 |
| 5,464,986 | 11/1995 | Boettcher et al. | 250/459.1 |
| 5,633,170 | 5/1997 | Neti | 436/118 |
| 5,753,185 | 5/1998 | Mathews et al. | 422/94 |
| 5,756,360 | 5/1998 | Harvey et al. | 73/23.31 |

FOREIGN PATENT DOCUMENTS

| | | |
|---|---|---|
| 0 209 295 A1 | 7/1996 | European Pat. Off. |
| 32 04 456 A1 | 2/1982 | Germany . |
| 37 07 622 A1 | 3/1987 | Germany . |
| 40 18 872 C2 | 6/1990 | Germany . |
| 44 24 370 A1 | 7/1994 | Germany . |
| 195 05 415 A1 | 8/1996 | Germany . |

*Primary Examiner*—Jill Warden
*Assistant Examiner*—S. Carrillo
*Attorney, Agent, or Firm*—Oppenheimer Wolff & Donnelly LLP

[57] ABSTRACT

A method and apparatus for detecting $NO_x$ by chemiluminescence. The apparatus includes a sample gas line having an inlet port for receiving a sample gas, a $NO_x$ converter connected to the sample gas line, a $N_2$ diluting gas line connected to the sample gas line upstream from the $NO_x$ converter, a bypass exhaust lie connected to the sample gas line, and a chemiluminescence analyzer connected to the $NO_x$ converter. The sample gas, which contains a $NO_x$ component, is introduced to the sample gas line through an inlet portion. The sample gas is diluted with nitrogen gas from the nitrogen diluting gas line, and the $NO_x$ component in the sample gas is converted to NO by the $NO_x$ converter. The chemiluminescence analyzer detects the $NO_x$ component.

4 Claims, 1 Drawing Sheet

GAS ANALYZER AND METHOD FOR DETECTING $NO_x$

FIELD OF THE INVENTION

The present invention relates to a sample diluting method in a chemiluminescence analyzer for measuring, for example, a nitrogen oxide component ($NO_x$) in exhaust gas from automobiles under atmospheric conditions.

BACKGROUND OF THE INVENTION

In the chemiluminescence analyzer for measuring exhaust gas from automobiles, dilution is carried out to lower the concentration of $CO_2$ or $H_2O$ in the sample gas in a reactor to reduce quenching action caused by these gases.

For the diluting gas, $O_2$ gas, which is the source gas of the ozone generator, is used, and a mixing point a of the diluting gas is installed, for example, at the downstream side of a $NO_x$ converter c in a sample gas line b, as shown in FIG. 2. In FIG. 2, letter d denotes a sample gas inlet; e, a filter; f, an atmospheric chemiluminescence analyzer; g, a deozonizer (ozone decomposer); h, a flow sensor; i, a sample gas outlet; j, an $O_2$ gas inlet; k, a diluting gas line; and l, an ozonizer (ozone generator).

As described above, if the diluting gas mixing point a is installed at a location downstream of the $NO_x$ converter c, by-products generated by a same specific component (e.g., high boiling-point hydrocarbons) in the exhaust gas may deposit in the sample gas line b between the mixing point a and the $NO_x$ converter c and clog the piping after the components pass the $NO_x$ converter c.

SUMMARY OF THE INVENTION

This invention has been made under these circumstances, and purports to provide a sample diluting method of the chemiluminescence analyzer in which the amount of by-products generated when a same specific component in the sample gas flows into the $NO_x$ converter can be reduced.

This invention forms a means for solving the above-mentioned problem as follows. A sample diluting method of chemiluminescence analyzer for allowing a sample gas to pass through a $NO_x$ converter, converting a $NO_x$ component in the sample gas into NO, and detecting the $NO_x$ component by chemiluminescence method is characterized in that $N_2$ gas for diluting the sample gas is introduced upstream of the $NO_x$ converter in the sample gas line for introducing the sample gas.

Because the sample gas introduced into the $NO_x$ converter is diluted, the amount of by-products itself generated by the specific component is reduced, and clogging of the piping downstream of the $NO_x$ converter can be effectively prevented.

Other aspects, features, and advantages of the present invention will become apparent to those persons having ordinary skill in the art to which the present invention pertains from the following description taken in conjunction with the accompanying drawings.

DETAILED DESCRIPTION OF THE PREFERRED EMBODIMENTS

Figure 1:
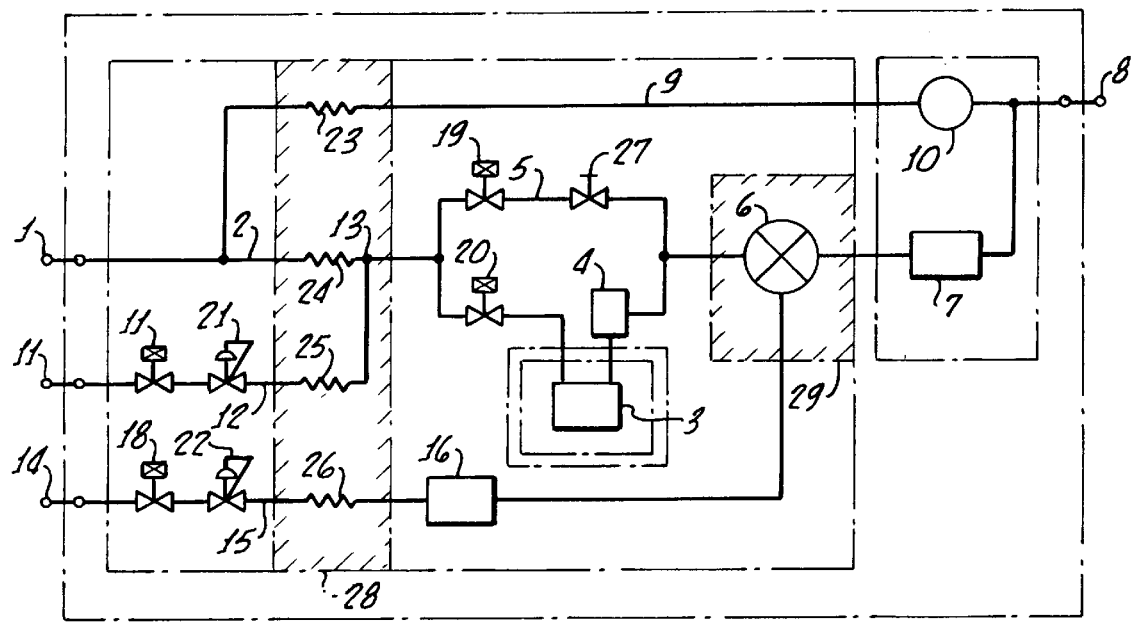
FIG. 1 is a block diagram showing an exemplary embodiment of a system for implementing a sample diluting method of a chemiluminescence analyzer according to this invention.
Figure 2:
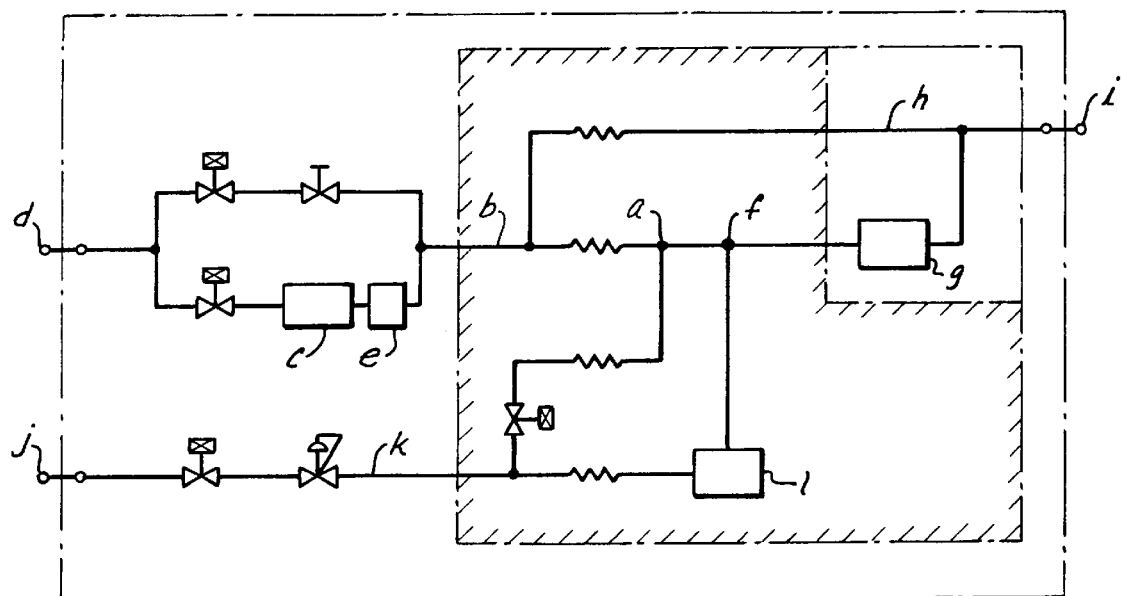
FIG. 2 is a block diagram showing an example of conventional atmospheric chemiluminescence analyzer.

Referring now to the drawings, an embodiment of a sample diluting method of a chemiluminescence analyzer according to this invention is described in detail.

FIG. 1 shows a configuration of an atmospheric chemiluminescence analyzer. Numeral 1 indicates a sample gas inlet for introducing sample gas such as automobile exhaust gas, etc. Numeral 2 indicates a $NO_x$ sample gas line. Numeral 3 indicates a $NO_x$ converter for converting $NO_x$ components to NO. Numeral 4 indicates a filter. Numeral 5 indicates a NO sample gas line. Numeral 6 indicates an atmospheric chemiluminescence analyzer. Numeral 7 indicates a deozonizer. Numeral 8 indicates a sample gas outlet. Numeral 9 indicates a bypass exhaust line. Numeral 10 indicates a flow sensor.

Numeral 11 indicates a diluting gas inlet port; numeral 12 a diluting gas line; numeral 13, a mixing point from $N_2$ gas line 12 to sample gas line 2; numeral 14, an $O_2$ gas inlet; numeral 15, an $O_2$ gas line; numeral 16, an ozonizer (ozone generator); numerals 17–20, solenoid valves; numerals 21 and 22, regulators; numerals 23–26, capillaries; numeral 27, a needle valve; and numerals 28 and 29, 50° C. temperature control areas.

Because $N_2$ gas is designed to mix with the sample gas upstream of the $NO_x$ converter 3 in this way, the consumption rate of expensive $O_2$ gas can be reduced. Further, as the $N_2$ gas does not lower the efficiency of $NO_x$ converter 3, degradation in performance of $NO_x$ converter 3 can be effectively prevented.

Because of the dilution effects of the sample gas by the $N_2$ gas can reduce the amount of by-products generated with a same specific component (e.g., high-boiling-point hydrocarbons) at the $NO_x$ converter 3, clogging of piping extending to the atmospheric chemiluminescence analyzer 6 can be suppressed, thereby improving maintainability. At the same time, the reduction of by-products also achieves a stable indication, thereby improving the detection accuracy.

$N_2$ is used for the diluting gas because if $O_2$ or air is used, $O_2$ becomes in excess in the $NO_x$ converter 3, and it is feared that the efficiency of the $NO_x$ converter 3 may be decreased, etc. In addition, $N_2$ which is free of oxidation is used.

The above-mentioned $N_2$ gas may be adjusted, for example, to 0.6 kgf/cm$^2$ and mixed with the sample gas downstream of the capillary 24. The solenoid valve 17 may be turned on only during measurement and calibration.

As described above, according to the sample diluting method of the chemiluminescence analyzer, because the sample gas is introduced into the $NO_x$ converter after it is diluted with $N_2$ gas, the consumption rate of expensive $O_2$ gas can be reduced, and, at the same time, by-products generated at the $NO_x$ converter can also be reduced. This can reduce clogging of piping and improve the maintainability, resulting in stability of indication and improvement in the detection accuracy.

Those skilled in the art will understand that the embodiments of the present invention described above exemplify the principles of the invention and do not limit the scope of the invention to those embodiments of the invention specifically illustrated in the drawings and described above. The exemplary embodiments provide a foundation from which numerous alternatives and modifications may be made, which alternatives and modifications are also within the scope of the present invention as defined in the appended claims. With reference to the following claims, unless the claims specifically use language directed to a "means" for performing a particular function, the claims are not intended to be limited to the structure specifically described and illustrated herein, but rather shall be construed to embrace all corresponding structure and equivalents thereof.

What is claimed is:

1. A method for diluting a sample gas in a chemiluminescence analyzer including a $NO_x$ converter connected to a sample gas line, said method comprising the steps of:

provide the sample gas to the $NO_x$ converter through the sample gas line;

introducing $N_2$ gas to the sample gas line upstream of the $NO_x$ converter to dilute the sample gas;

providing a bypass exhaust line which is connected to said sample gas line upstream of introducing the $N_2$ gas to said sample gas line;

converting a $NO_x$ component in the sample gas into NO; and detecting the $NO_x$ component by chemiluminescence.

2. The method of claim 1, wherein the sample gas is an exhaust gas from an automobile.

3. A gas analyzer for detecting a $NO_x$ component in a sample gas, said analyzer comprising:

a sample gas line including an inlet port for receiving the sample gas;

a $NO_x$ converter connected to said sample gas line for converting a $NO_x$ component in the sample gas to NO;

a $N_2$ diluting gas line connected to said sample gas line upstream from said $NO_x$ converter and including an inlet port for receiving $N_2$ gas for diluting the sample gas;

a bypass exhaust line connected to said sample gas line, wherein said bypass exhaust line is connected to said sample gas line upstream of said $N_2$ diluting gas line; and a chemiluminescence analyzer connected to said $NO_x$ converter for detecting the $NO_x$ component.

4. The gas analyzer of claim 3, wherein the sample gas is an exhaust gas from an automobile.

* * * * *